US009968548B2

(12) United States Patent
DuBourdieu et al.

(10) Patent No.: US 9,968,548 B2
(45) Date of Patent: May 15, 2018

(54) DENTAL HARD CHEW SUPPLEMENTS CONTAINING ANTIMICROBIAL ACTIVES

(71) Applicant: Vets Plus, Inc., Menomonie, WI (US)

(72) Inventors: Daniel DuBourdieu, Limerick, ME (US); Rajiv Lall, Menomonie, WI (US); Ajay Srivastava, Menomonie, WI (US)

(73) Assignee: VETS PLUS, INC., Menomonie, WI (US)

(*) Notice: Subject to any disclaimer, the term of this patent is extended or adjusted under 35 U.S.C. 154(b) by 144 days.

(21) Appl. No.: 14/934,870

(22) Filed: Nov. 6, 2015

(65) Prior Publication Data

US 2016/0128932 A1 May 12, 2016

Related U.S. Application Data

(60) Provisional application No. 62/076,588, filed on Nov. 7, 2014.

(51) Int. Cl.

| | |
|---|---|
| *A61K 8/98* | (2006.01) |
| *A61K 8/67* | (2006.01) |
| *A61K 8/35* | (2006.01) |
| *A61K 8/19* | (2006.01) |
| *A61Q 11/00* | (2006.01) |
| *A61K 8/26* | (2006.01) |
| *A61K 8/27* | (2006.01) |
| *A61K 8/81* | (2006.01) |
| *A23K 20/174* | (2016.01) |
| *A23K 20/111* | (2016.01) |
| *A23K 20/158* | (2016.01) |
| *A23K 20/163* | (2016.01) |
| *A23K 20/10* | (2016.01) |
| *A23K 20/20* | (2016.01) |
| *A23K 50/42* | (2016.01) |

(52) U.S. Cl.
CPC ............ *A61K 8/988* (2013.01); *A23K 20/10* (2016.05); *A23K 20/111* (2016.05); *A23K 20/158* (2016.05); *A23K 20/163* (2016.05); *A23K 20/174* (2016.05); *A23K 20/20* (2016.05); *A23K 50/42* (2016.05); *A61K 8/19* (2013.01); *A61K 8/26* (2013.01); *A61K 8/27* (2013.01); *A61K 8/35* (2013.01); *A61K 8/67* (2013.01); *A61K 8/671* (2013.01); *A61K 8/673* (2013.01); *A61K 8/675* (2013.01); *A61K 8/676* (2013.01); *A61K 8/678* (2013.01); *A61K 8/8147* (2013.01); *A61Q 11/00* (2013.01); *A61K 2800/413* (2013.01)

(58) Field of Classification Search
CPC .................... A23K 1/18; A61K 7/18
USPC ............................... 426/132, 576
See application file for complete search history.

(56) References Cited

U.S. PATENT DOCUMENTS

| | | | |
|---|---|---|---|
| 6,178,922 B1* | 1/2001 | Denesuk | A01K 1/0152 119/710 |
| 6,228,402 B1 | 5/2001 | Wolf et al. | |
| 8,455,007 B2 | 6/2013 | Ballot-Flurin | |
| 2003/0219516 A1* | 11/2003 | Pater | A01K 15/026 426/132 |
| 2005/0008861 A1* | 1/2005 | Yadav | C08K 3/08 428/403 |
| 2005/0260306 A1* | 11/2005 | Baldus | A23K 10/30 426/132 |
| 2010/0003393 A1* | 1/2010 | Torney | A01K 15/026 426/576 |
| 2010/0254915 A1 | 10/2010 | Kao | |
| 2013/0280183 A1* | 10/2013 | Salazar Navarrete | A61K 8/37 424/52 |
| 2014/0271757 A1* | 9/2014 | Agrawal | C09K 8/524 424/405 |
| 2015/0044266 A1 | 2/2015 | Fetissova et al. | |

FOREIGN PATENT DOCUMENTS

| | | | |
|---|---|---|---|
| CA | 1331447 | * 12/1987 | ............... A23K 1/18 |
| CN | 1442130 A | 9/2003 | |
| WO | WO 2013163714 A1 | 11/2013 | |

OTHER PUBLICATIONS

Besinis A, et al. "Inhibition of biofilm formation and antibacterial properties of a silver nano-coating on human dentine." Nanotoxicology. Nov. 2014; 8(7):745-54.
Galdiero, S. et al. "Silver Nanoparticles as Potential Antiviral Agents." Molecules 2011, 16, 8894-8918.
Grindel B. and I. Olsen. "The role of viruses in oral disease." Journal of Oral Microbiology 2010. 2: 2127.
Ikeno K., et al. "Effects of propolis on dental caries in rats," Caries Research, vol. 25, No. 5, pp. 347-351, 1991.
Kim, Jun Sung, et al. "Antimicrobial effects of silver nanoparticles." Nanomedicine: Nanotechnology, Biology, and Medicine 3 (2007) 95-101.
Koo H, et al. "Effect of a mouth rinse containing selected propolis on 3-day dental plaque accumulation and polysaccharide formation." Caries Research 2002; 36(6):445-448.
Kvitek L., et al. "Antibacterial activity and toxicity of silver— nanosilver versus ionic silver." Journal of Physics: Conference Series 304 (2011).
Mali, A. M. et al. "Comparative evaluation of 0.1% turmeric mouthwash with 0.2% chlorhexidine gluconate in prevention of plaque and gingivitis: A clinical and microbiological study." J. Indian Soc. Periodontol. Jul. 2012; 16(3):386-91.
Pereira EM, et al. "Clinical Evidence of the Efficacy of a Mouthwash Containing Propolis for the Control of Plaque and Gingivitis: A Phase II Study." Evidence-Based Complementary and Alternative Medicine 2011; 2011:750249.

(Continued)

*Primary Examiner* — Walter E Webb

(74) *Attorney, Agent, or Firm* — Charles S. Sara; DeWitt Ross & Stevens S.C.

(57) ABSTRACT

A hard chew matrix containing antimicrobial actives, such as nanosilver, curcumin and propolis for use in dogs and other animals is disclosed.

20 Claims, No Drawings

(56) References Cited

OTHER PUBLICATIONS

Muglikar, et al. "Efficacy of curcumin in the treatment of chronic gingivitis: a pilot study." Oral Health Prev. Dent. 2013; 11(1):81-6.
Santos VR. "Propolis: Alternative Medicine for the Treatment of Oral Microbial Diseases" http://dx.doi.org/10.5772/54003.
Stebounova LV, et al. "Nanosilver induces minimal lung toxicity or inflammation in a subacute murine inhalation model." Part. Fibre Toxicol. Jan. 25, 2011; 8(1):5. doi: 10.1186/1743-8977-8-5.
Waghmare PF, et al. "Comparative evaluation of turmeric and chlorhexidine gluconate mouthwash in prevention of plaque formation and gingivitis: a clinical and microbiological study." J. Contemp. Dent. Pract. 2011; 12(4):221-4.
Więckiewicz W., et al. "Does Propolis Help to Maintain Oral Health?" Evidence-Based Complementary and Alternative Medicine. vol. 2013 (2013), Article ID 351062, 8 pages. http://dx.doi.org/10.1155/2013/351062.

* cited by examiner

DENTAL HARD CHEW SUPPLEMENTS CONTAINING ANTIMICROBIAL ACTIVES

CROSS-REFERENCE TO RELATED APPLICATIONS

This application claims priority under 35 USC § 119(e) to U.S. Provisional Patent Application 62/076,588 filed Nov. 7, 2014, the entirety of which is incorporated herein by reference.

BIBLIOGRAPHY

Complete bibliographical citations to the documents cited herein can be found in the Bibliography, immediately preceding the claims.

FIELD OF THE INVENTION

The invention relates to hard chews for animals. The present invention further relates to dental hard chews that contain plaque, tartar, halitosis and gum inflammation reducing active ingredients.

BACKGROUND

Tooth and gum disease can lead to serious health problems in companion animals. Dogs and cats tend to significantly use their teeth when chewing on foodstuffs. Therefore, gum disease and loss of teeth can all have serious consequences for companion animals. Damage to the teeth and gums in companion animals is considered to be permanent. According to the American Veterinary Dental Society, 80% of dogs and 70% of cats have periodontal (gum) disease by the age of three. Proper dental care could increase the life of these animals by many years. Within that context, maintenance of good oral health and prevention of oral disease is a primary necessity for animals. However, pet owners have to provide that necessity.

Dog teeth and gums are also susceptible to many of the same oral health problems as humans. This includes plaque buildup, dental tartar (calculus), gingivitis and various periodontal diseases. The survival of pathogenic bacteria in the oral cavity depends on their successful adhesion to dental surfaces and their ability to develop into biofilms, known as dental plaque. This can eventually solidify into tartar (calculus) on the teeth. Bacteria from the dental plaque are responsible for the development of dental caries, gingivitis, periodontitis, stomatitis and peri-implantitis. The mouth environment is rich in bacterial flora which in some conditions may lead to such diseases like caries or diseases of periodontium or even halitosis. The basic role in development of dental caries plays *Streptococcus mutans* and, to a lower degree, *Lactobacillus* sp. Cariogenic influence of other bacteria including *Streptococcus, Enterococcus*, or *Actinomyces* is well known. Virulence of *Streptococcus mutans* results from its adhesion, acid-forming properties, and tolerance to environment with low pH.

Bacterial flora of the mouth can cause not only caries but also periodontal disease. Bacterial plaque accumulated over and under gums contributes to inflammation of the tissues adjacent to teeth which leads to clinical attachment loss and a loss of alveolar process. Microbes which are located in the subgingival plaque are divided into five complexes. One of them, the "red complex" made up of *Tannerella forsythensis, Porphyromonas gingivalis*, and *Treponema denticola*, has strong relation with an increased depth of periodontal pockets and with a bleeding on probing. *Prevotella intermedia* and *Fusobacterium nucleatum* are also main microbiota involved in periodontal disease related to plaque. A decrease of the number of these pathogenic microbes could potentially influence epidemiology of periodontal diseases by a limitation of their number and intensity.

The first stage of periodontal disease is gingivitis, which is very common. In this stage, the bacteria have mixed with saliva and formed plaque. Plaque adheres to the teeth and hardens, forming tartar and calculus. These tartar deposits irritate the gum tissue and cause inflammation, swelling, and infection. It is at this stage that gingivitis is most notable. It is important to the overall health of the dog that proper dental care is provided before bacteria and/or their toxins to enter the bloodstream with potentially deleterious effects on various internal organs. Conversely, poor systemic health may manifest in the oral cavity in various ways and may also exacerbate periodontal disease.

While bacteria have traditionally been the focus of oral diseases, viruses play a significant role in these diseases as well (Grindel). The role of several viruses in ulceration is well known, but viruses of the herpes family may play a role in periodontitis, and papillomaviruses are probably involved in oral cancer. Anti-herpes medication may, in some cases, be relevant in treating periodontitis, while papillomavirus vaccine would be expected to decrease the prevalence of oral cancer.

With many of the oral diseases, there is little recourse available to the pet owner. If an oral disease is diagnosed early enough, aggressive and regular oral cleaning may eventually clear up the problem. A veterinarian and/or pet owner may have to clean the pet's oral cavity several times a week for months or for the duration of the animal's life. This is typically done by brushing or scraping the teeth and gums and may require a sedated animal in order to not get bitten. The brushing option requires considerable input in time, effort or money from the pet owner.

Attempts to prevent dental diseases in companion animals through the use of hard chews has been a partial answer for pet owners who do not wish to get bitten when cleaning the teeth of an animal. Chewing is very important for dog's oral health. It keeps the dog's teeth clean through physical scraping of a harden matrix against the teeth to remove plaque and tartar buildup. It is a natural behavior of dogs to chew on a variety of objects that allows for hard substances including natural and artificial matrixes to be used to help remove plaque.

In the last 20 years, digestible hard chews made out of starch or grains became available that have some nutritional value by providing vitamins, minerals and other certain botanical extracts that may help with keeping the breath of the animal fresh. The trend is towards chews that can have some nutritional value besides the traditional use of keeping teeth clean and satisfying the urge to chew by dogs. The annual total hard chew market in the USA is around $500,000,000. As the trend is towards digestible chews, having the ability to incorporate plaque reducing actives into a digestible hard chew represents advancement in the field and will be a competitive advantage. However, the hard chews on the market do not contain plaque reducing actives.

Dog hard chews come in a variety of materials and are generally used as a method to keep the dog's teeth clean while satisfying the normal ongoing chewing behavior associated with dogs. Dog chews fall into 3 general categories based on their composition. They can be made from animal, plant or from artificial ingredients. Examples of chews being made of animal-derived parts or ingredients include bull penis, cheese, deer antler, fish skin, rawhide, pig ears, cow hooves and real bones. Plant-based chews can be based on various plant starches, dried yam, and sweet potato. Artificial ingredients for creating chews can include rubber, nylon and thermoplastics. The hard chews made out of plastic-like materials can last for months; however, these are not digestible. The hard chews made out of animal or plant materials are digestible. This digestible hard chew will typically last perhaps through 30 minutes of chewing and can help keep teeth clean while providing vitamins and minerals to the animal.

However, the concept of a digestible hard chew of any composition category as an option to improve health of the dog would be greatly improved if antimicrobial agents that reduce plaque in an active manner were incorporated into the digestible hard chew format. This would allow the dog to not only get benefits of teeth cleaning and satisfying normal chewing behavior but also reduce plaque through active killing mechanisms of bacteria rather than physical removal mechanisms.

While hard chew formats have been used in attempts to help maintain oral health in companion animals, they can be improved by the addition of antimicrobial actives. Therefore, there is a need for hard chew compositions for maintaining good oral health as well as preventing and treating oral disease in companion animals by the addition of plaque removing ingredients.

SUMMARY OF THE INVENTION

The present invention is directed to a dental hard chew supplement comprised of a hard chew matrix, either edible or nonedible, containing at least one antimicrobial active ingredient, selected from the group consisting of nanosilver, curcumin and propolis to reduce plaque and gum inflammation, wherein the antimicrobial active ingredient is present in or on a hard chew matrix. The hard matrix chew helps remove plaque by physical actions of chewing by the pet. The antimicrobial active ingredient released from the matrix while chewing can help reduce plaque by actively killing the organisms that cause plaque buildup. A reduction in gum inflammation occurs with the use of curcumin found the invention. Thus, gum health will be improved by use of the invention.

Specifically, the present invention is directed to a dental hard chew supplement for treating tooth and gum health issues in a mammal comprising a therapeutically effective amount of an antimicrobial active ingredient, wherein the antimicrobial active ingredient is present in or on a hard chew substrate matrix.

The present invention is further directed to dental hard chew supplement for treating tooth and gum health issues in a mammal comprising: a therapeutically effective amount of an antimicrobial active ingredient, wherein the antimicrobial active ingredient comprises: (i) silver nanoparticles of elemental silver, silver ions or silver salts administered in an amount of from about 1 mg/kg body weight of the mammal to about 30 mg/kg body weight of the mammal, (ii) curcumin administered in an amount of from about 10 mg/kg body weight of the mammal to about 20 mg/kg body weight of the mammal, and (iii) propolis administered in an amount of from about 0.001 mg/kg body weight of the mammal to about 10,000 mg/kg body weight of the mammal. The dental hard chew supplement further comprises vitamins in therapeutically effective amounts selected from the group consisting of vitamin A, vitamin C, vitamin D, vitamin E, vitamin K, vitamin B1, vitamin B2, vitamin B3, vitamin B5, vitamin B6, vitamin B7, vitamin B9 and vitamin B12, wherein the vitamins are present in amounts from about 0.5% to about 1% w/w; minerals in therapeutically effective amounts selected from the group consisting of zinc, manganese, copper and molybdenum; and omega-3 and omega-6 polyunsaturated fatty acids in therapeutically effective amounts, wherein the antimicrobial active ingredient is present in or on a hard chew substrate matrix.

Still further, the present invention is directed to a method of treating oral gum disease in a mammal comprising administering to the mammal a dental hard chew supplement comprising a therapeutically effective amount of an antimicrobial active ingredient, wherein the antimicrobial active ingredient comprises (i) silver nanoparticles of elemental silver, silver ions or silver salts administered in an amount of from about 1 mg/kg body weight of the mammal to about 30 mg/kg body weight of the mammal, (ii) curcumin administered in an amount of from about 10 mg/kg body weight of the mammal to about 20 mg/kg body weight of the mammal, and (iii) propolis administered in an amount of from about 0.001 mg/kg body weight of the mammal to about 10,000 mg/kg body weight of the mammal; vitamins in therapeutically effective amounts selected from the group consisting of vitamin A, vitamin C, vitamin D, vitamin E, vitamin K, vitamin B1, vitamin B2, vitamin B3, vitamin B5, vitamin B6, vitamin B7, vitamin B9 and vitamin B12, wherein the vitamins are present in amounts from about 0.5% to about 1% w/w; minerals in therapeutically effective amounts selected from the group consisting of zinc, manganese, copper and molybdenum; and omega-3 and omega-6 polyunsaturated fatty acids in therapeutically effective amounts, wherein the antimicrobial active ingredient is present in or on a hard chew substrate matrix.

The present invention significantly advances the art of plaque removal and reduction of gum inflammation in companion animals through a novel combination of ingredients that actively kill microbes that cause plaque buildup. The invention places these active ingredients into a hardened matrix that companion animals chew and combines the physical plaque removal processes from the harden matrix with the active killing processes from the active ingredients. Combining physical scraping actions by hardened chew matrixes with active plaque reducing agents represents a novel approach and advances the art to plaque reduction in companion animals.

The present invention contains metals like silver ions and silver nanoparticles, curcumin and propolis that are not destroyed by elevated temperatures used in the manufacture of extrusion processes. The present invention contains a novel combination of active ingredients that helps reduce plaque and reduce gum inflammation. The choice of plaque removing ingredients to be used in the invention has been selected to be silver ions and nano-sized silver, curcumin and propolis since they are good alternatives to chlorhexidine. Chlorhexidine, while considered the gold standard in dentistry for the prevention of dental plaque, was flagged in 2012 due to its potential to induce anaphylactic reactions. The challenge has been to find safer alternatives than chlorhexidine.

The objects and advantages of the invention will appear more fully from the following detailed description of the preferred embodiment of the invention.

DETAILED DESCRIPTION OF THE INVENTION

The present invention employs the use of a dental hard chew supplement for companion animals and an active antimicrobial ingredient sufficient to reduce plaque, and reduce gum inflammation.

The structural integrity of the dental hard chew supplement of the present invention is supported by a hard chew substrate matrix, otherwise known as a "hard chew," which can either be digestible or indigestible to the mammal. As described previously, the hard chew can come in a variety of materials and is generally used as a method to keep teeth clean while satisfying the normal ongoing chewing behavior associated with mammals. These types of hard chews typically fall into 3 general categories based on their composition. They can be made from animal-derived parts, plants or from artificial ingredients. The hard chews made out of animal or plant materials are digestible. This digestible hard chew will typically last perhaps through 30 minutes of chewing and can help keep teeth clean while providing vitamins and minerals to the animal.

Substrate Matrix for a Plant-Based Hard Chew:

Plant-based chews can be based on various plant starches, dried yam, and sweet potato. The hard edible plant-based substrate material may be formed by any one or more of the following ingredients: soy flour, wheat gluten, pregel wheat flour, wheat feed flour, corn starch, soy protein concentrate, oat, barley, brown rice, dried whey powder, liver powder, carrot powder, cherry powder, pineapple powder, and/or alfalfa herb powder. The carrier can include dehydrated meat byproducts and mixed with the flour and a fluid lubricant. In addition, the flours may be whole flours or flours which have had fractions removed; for example, the germ fraction or the husk fraction may be removed. The carrier source will be chose largely on the basis of digestibility, the nutritional value, palatability considerations, and the type of ultimate product desired.

As the final hard chew product can be digestible, the base ingredients of the hard chew can contain digestible starch and/or starch-like material. As used herein, "starch" refers to any substance comprised of more than about 80%, 90%, 95%, or even 100% polysaccharides by weight. Starches from various sources are known in the art. Examples of such ingredients include cereal, grains or flours obtained upon grinding cereal grains such as corn, oats, wheat, milo, barley, rice and others. Other sources of ingredients include tuberous foodstuffs, such as potatoes, tapioca, and the like. Starch quantities between 1% and 50%, preferably between 10% and 40%, and especially preferably between 15% and 30%, are employed in this invention. The percentages are percent by weight of the finished composition.

Emulsifier:

Emulsifiers which can be employed in the plant-based hard chew are selected from groups including nonionic surfactants, e.g., polyoxyethylated castor oil, polyoxyethylated sorbitan monooleate, sorbitan monostearate, ethyl alcohol, glycerol monostearate, polyoxyethyl stearate, alkylphenol polylglycol ethers; and ampholytic surfactants, e.g., disodium N-lauryl-B-iminodipropionate or lecithin; or anionic surfactants, such as sodium lauryl sulphate, fatty alcohol ether sulphates, mono-dialkyl polyglycol ether orthophosphoric ester monoethanolamine salt.

The quantities employed here preferably amount to anywhere between 0 and 20% by weight based on the total amount of constituents. Quantities of from 4% to 16% by weight are preferred, and quantities of from 6% to 8% by weight are especially preferred.

Softening Agents:

In order provide an appropriate medium for mixing all of the ingredients together in the plant-based hard chew, softening agents may be utilized. Examples of suitable softening agents include water, glycerol and propylene glycol, wetting agents such as cetyl alcohol and glycerol monostearate, and other humectants, such as oat fiber. Glycerol monostearate is a preferred softening agent. The softening agent may be included in an amount of from 0% to about 50% w/w of the hard chew substrate matrix, with preferred amounts between 5% and 25% and especially preferred amounts between 9% and 11%.

Flavorings and Sweeteners:

Flavorings and sweeteners are preferably present in the plant-based hard chew of the present invention. All flavorings and sweeteners must be of at least food grade quality. The composition can include such additives as sweeteners and flavorings. Sweeteners can be selected from a wide variety of suitable materials known to the art. Representative and non-limiting examples of sweeteners include xylose, ribose, sucrose, mannose, galactose, fructose, dextrose, maltose, and mixtures thereof. Natural sweeteners such as sugar and molasses to name a few may be used. In addition to natural flavorings, other non-animal flavorings can include, for example, anise oil, carob, peanuts, fruit flavors, other sweeteners such as honey and maple syrup, herbs such as parsley, celery leaves, peppermint, spearmint, garlic, or combinations thereof. Natural and synthetic flavor oils can also be used. Examples include spearmint oil, peppermint oil, cinnamon oil, wintergreen oil, citrus oils, including lemon, orange, grape, lime and grapefruit, and other fruit essences including apple, strawberry, cherry, pineapple, and others that are familiar to the art. Natural flavors, such as chicken liver, can be used. Quantities of between 0% and 20%, preferably between 2% and 10%, and especially preferably between 4% and 6% are employed in this invention. The percentages are percent by weight of the finished composition.

Vitamins:

The plant-based hard chew may include one or more vitamins. Vitamins are necessary for literally tens of thousands of different chemical reactions in the body. They often work in conjunction with minerals and enzymes to assure normal digestion, reproduction, muscle and bone growth and function, healthy skin and hair, clotting of blood, and the use of fats, proteins, and carbohydrates by the body. For example, vitamin E isomers (mixed tocopherols) are antioxidants that help protect animals from free radical damage. Vitamin deficiencies can occur in an animal if poor quality food is provided to the animal. Vitamin deficiencies can also occur if an animal is under stress. Ill or recovering animals that may have a poor appetite typically need a vitamin supplement since they are not receiving their daily requirements through the food they eat. Animals in other situations such as stress from travel, showing, training, hunting, breeding, or lactation can also benefit from vitamin supplementation. Older animals can also benefit from vitamin supplementation. Older animals tend to absorb fewer vitamins, minerals, and electrolytes through the intestinal tract, and lose more of them through the kidneys and urinary tract. Also, some older animals eat less (due to conditions such as oral disease) and may not receive their daily needs of vitamins and minerals. These same old animals are often the ones that will also be given solid medications to treat other conditions. Another issue that may increase the need for vitamin supplementation in animals is that commercial feeds typically involve a heating process that can destroy vitamins present in the feed.

Any vitamin known in the art may be included in the composition of the present invention. Particular vitamins may be provided according to the nutritional requirements of the target animal. Suitable vitamins include both water soluble and/or fat soluble vitamins. Exemplary water soluble vitamins include any or all of the B vitamins (Vitamin $B_1$, $B_2$, $B_3$, $B_4$, $B_5$, $B_6$, $B_7$, $B_8$, $B_9$, $B_{10}$, $B_{11}$, and $B_{12}$) and/or Vitamin C (ascorbic acid). Exemplary fat soluble vitamins include Vitamin A, Vitamin D, Vitamin E, and Vitamin K. The amount of the vitamins included in the substrate matrix can be adapted to the specific needs of the target animal. As an example, each vitamin may be included in an amount of from about 0.001% to about 10.0% w/w of the viscoelastic mass, preferably from about 0.01% to about 5.0% w/w, and more preferably from about 0.5% to about 1% w/w.

Minerals:

Minerals play important roles in many biochemical functions in the body and can be incorporated into the plant-based hard chew. Deficiencies of minerals can lead to problems in the immune system. However supplementation of zinc and copper can help correct these problems. As absorption of chelated minerals to amino acids or other substances is enhanced, this invention uses chelated minerals. This invention uses chelated copper, zinc, manganese and molybdenum to benefit the immune system. The preferred concentration of copper is from 0.1 mg to 2 mg/kilogram; for zinc is from 100 mg to 300 mg/kilogram; and for manganese is from 0.05 mg to 0.2 mg/kilogram.

Polyunsaturated Fatty Acids:

Omega-3 and omega-6 fatty acids (also called ω-3 and ω-6 fatty acids or n-3 and n-6 fatty acids) are polyunsaturated fatty acids (PUFAs) with a double bond (C=C) at the third or sixth carbon atom from the end of the carbon chain for the omega 3 and omega 6, respectively. The fatty acids have two ends, the carboxylic acid (—COOH) end, which is considered the beginning of the chain, thus "alpha", and the methyl (CH3) end, which is considered the "tail" of the chain, thus "omega." The way in which a fatty acid is named is determined by the location of the first double bond, counted from the methyl end, that is, the omega (ω-) or the n-end.

The three types of omega-3 fatty acids involved in mammalian physiology are α-linolenic acid (ALA), found in plant oils, eicosapentaenoic acid (EPA), and docosahexaenoic acid (DHA), both commonly found in marine oils. Marine algae and phytoplankton are primary sources of omega-3 fatty acids. Common sources of plant oils containing the omega 3 ALA fatty acid include walnut, edible seeds, clary sage seed oil, algal oil, flaxseed oil, Sacha Inchi oil, Echium oil, and hemp oil, while sources of animal omega-3 EPA and DHA fatty acids include fish oils, egg oil, squid oils, and krill oil. Omega 3 and omega 6 fatty acids are selected from the group consisting of plant oils, fish oils, animal oils, algea sources and crustacean sources. Evening primrose oil is an excellent source of omega 6 polyunsaturated fatty acids. Linoleic acid (18:2, n-6), the shortest-chained omega-6 fatty acid, is one of many essential fatty acids and is categorized as an essential fatty acid because mammals cannot synthesize it. Mammalian cells lack the enzyme omega-3 desaturase and therefore cannot convert omega-6 fatty acids to omega-3 fatty acids.

The amount of omega 3 and omega 6 polyunsaturated fatty acids included in hard chew substrate matrix can be adapted to the specific needs of the target animal. As an example, omega 3 and omega 6 polyunsaturated fatty acids may be included in an amount of from about 0.001% to about 25% w/w of the viscoelastic mass, preferably from about 1.0% to about 20.0% w/w, and more preferably from about 8.0% to about 15.0% w/w.

Amounts of Components

The amounts of each of the components in the final product may be varied depending upon the nature of the ingredients, the weight and condition of the animal to be treated, and the unit dosage desired. Those of ordinary skill in the art will be able to adjust dosage amounts as required.

Substrate Matrix for Animal-Derived Hard Chew

Examples of hard chews made of animal-derived parts or ingredients include bull penis, hardened (dried) animal ligaments or rawhide, deer antler, cattle horns, fish skin, pig ears, cow hooves, real animal bones and the like.

Substrate Matrix for Hard Chew Made from Artificial Ingredient

Artificial ingredients for creating chews can include rubber, plastic, nylon and thermoplastics. The hard chews made out of plastic-like materials can last for months; however, these are not digestible.

Antimicrobial Active Agent:

Nano-Sized Metal Particle:

A nanoparticle consists of many atoms or ions clustered together to form a particle 1-100 nanometer (nm) in size. The term nanoparticle refers to a particle whose dimension is less than 100 nm. The metal particle of the invention is selected from the group consisting of silver, gold, aluminum, copper, and zinc. The metal particles range in size from about 0.1 nm to 200 nm. Preferably, the metal particles range in size from 0.1 nm to 100 nm. More preferably, the metal particles range in size from 0.1 nm to 10 nm. The preferred metal particles are nano-sized particles of elementary silver, silver ions or silver salts. Due to their small size, these nanoparticles are able to invade bacteria and other microorganisms and kill them. The term "silver nanoparticles" or "nanosilver" of the invention refers to particles made from elemental silver, silver ions or silver salts. However, the silver salts of the invention can also be found at a different scale sizes. The silver salts can exist as powders that can also be solubilized by water and exist as highly reactive individual silver ions. These silver ions are on the scale of an individual atom size, which is much smaller scale than the nanoscale.

The medicament is administered in a dose comprising about of 0.2 nM to 30 nM of nano-sized silver. Preferably, the silver nanoparticles are administered in an amount of from about 0.001 mg/kg body weight of the animal to about 10,000 mg/kg body weight of the animal. More preferably, the silver nanoparticles are administered in an amount from about 1 mg/kg body weight of the animal to about 200 mg/kg body weight of the animal. Most preferably, the silver nanoparticles are administered in an amount of from about 1 mg/kg body weight of the animal to about 30 mg/kg body weight of the animal.

The antibacterial effects of silver salts have been known since antiquity, and silver is currently used to control bacterial growth in a variety of applications, including dental work, catheters, and burn wounds. In fact, it is well known that silver ions and silver-based compounds are highly toxic to microorganisms, showing strong biocidal effects on as many as twelve species of bacteria including *E. coli*. The medicament is administered in a dose comprising about of 1 to 2 mg of silver ions or silver salts per Kg of invention. Preferably, the silver ions or silver salts is administered in an amount of from about 0.001 mg/kg body weight of the animal to about 10,000 mg/kg body weight of the animal. More preferably, the silver ions or silver salts is administered in an amount from about 0.01 mg/kg body weight of the animal to about 200 mg/kg body weight of the animal. Most preferably, the silver ions or silver salts is administered in an amount of from about 0.5 mg/kg body weight of the animal to about 9 mg/kg body weight of the animal.

The antimicrobial effects of silver (Ag) ion or salts are well known, but the effects of silver nanoparticles on microorganisms and antimicrobial mechanism are not fully understood. There appears to be variable results in the use of nanosilver particles for its efficacy against pathogenic microbes. For example, it was shown that yeast and E. coli were inhibited at the low concentration of silver nanoparticles, whereas the growth-inhibitory effects on Staphylococcus aureus were mild (Kim). Therefore it was unexpected that silver nanoparticles can help inhibit biofilm formation when applied to teeth. Silver nanoparticles may be a viable alternative to both chlorhexidine and silver nitrate, protecting from dental plaque (Besinis).

Silver nanoparticles have mainly been studied for their antimicrobial potential against bacteria, but have also proven to be active against several types of viruses including human immunodeficiency virus, hepatitis B virus, herpes simplex virus, respiratory syncytial virus, and monkey pox virus. The use of metal nanoparticles provides an interesting opportunity for novel antiviral therapies especially in dental applications for companion animals. Since metals may attack a broad range of targets in the virus (Galdiero) there is a lower possibility to develop resistance as compared to conventional antivirals.

There is increasing interest in the environmental and health consequences of silver nanoparticles as the use of this material becomes widespread. Various studies have shown that nanosilver can be safely used to kill bacteria and viruses at much lower concentrations than where acute toxicity to mammalian cells or eukaryotic organisms can occur. For example it was shown that antibacterial activity of silver nanoparticles had high antibacterial activity even at very low concentrations around several units of mg/L (Kvitek). These concentrations are comparable with concentrations of ionic silver revealing same antibacterial effect. However, such low concentrations of silver nanoparticles did not show acute cytotoxicity to mammalian cells. This occurs at concentrations higher than 60 mg/L of silver, while the cytotoxic level of ionic silver is much more lower (approx. 1 mg/L). Moreover, the silver nanoparticles exhibit lower acute ecotoxicity against the eukaryotic organisms such as *Paramecium caudatum, Monoraphidium* sp. and *D. melanogaster*. The silver nanoparticles are toxic to these organisms at the concentrations higher than 30 mg/L of silver. On the contrary, ionic silver retains its cytotoxicity and ecotoxicity even at the concentration equal to 1 mg/L. The performed experiments demonstrate significantly lower toxicity of silver nanoparticles against the eukaryotic organisms than against the prokaryotic organisms. (Kvitek)

Other studies have shown that mice exposed to silver nanoparticles showed minimal pulmonary inflammation or cytotoxicity following sub-acute exposures (Stebounova).

Curcumin:

The medicament may also contain curcumin, alone or in conjunction with the other antimicrobial actives. The curcumin is selected from natural derivatives of curcuminoids found in yellow turmeric and white turmeric, including curcumin, desmethoxycurcumin, bis-desmethoxycurcumin, tautomeric forms including 1,3-diketo forms and enol forms along with tetra hydro curcumins and in nano-sized particles. The curcumin is in a preferred concentration of 0.01% to 0.1% w/w in a hard chew format.

Certain food ingredients have been used since antiquity for remedying oral ailments. Turmeric is one such ingredient that has been used for remedying oral ailments, among other its therapeutic applications. It has been shown that turmeric mouthwash can be superior to chlorhexidine in the prevention of plaque and gingivitis when used as an adjunct to mechanical plaque control in humans (Mali). Turmeric contains approximately 3-4% curcumin by dry weight. This yellow pigmented polyphenol has been studied extensively in human clinical research as a natural alternative to the common mouthwash ingredient chlorhexidine for the treatment of gingivitis and inflammation of the gum tissue. However, chlorhexidine presents problems for anaphylactic shock. Clearly, safer alternatives are needed and especially if they can be shown to be superior. The use of curcumin allows for this.

One of the major differences with a turmeric (curcumin)-based mouthwash is that if one happened to swallow some, it would not result in the type of adverse effects associated with a biocidal/antiseptic chemical such as chlorhexidine. In fact, given the broad range of documented health benefits of turmeric, it would actually provide some side benefit, were this to happen. However, mouthwashes are not practical for companion animals since they would be simply swallowed. An improved approach would be to incorporate the curcumin into a hard chew format that allows for the curcumin to be slowly released and maintained in the mouth for longer periods of time before swallowed while the physical scrapping aspects can occur to also remove plaque. Once the curcumin is swallowed additional health benefits would be expected.

Most preferably, the curcumin is administered in an amount of from about 10 mg/kg body weight of the animal to about 20 mg/kg body weight of the animal.

Propolis:

The medicament may also contain propolis or any derivative from propolis, alone or in conjunction with the other antimicrobial actives. The propolis is selected from crude material, propolis extracts using water, ethanol, glycol or olive oil extraction processes. Propolis is a wax-cum-resin substance that is produced by bees. It was used in medicine in ancient Egypt. Propolis is made from substances collected by bees from tree buds which are then digested and mixed with the substance secreted by bee's glands. It is dark green or brown and its chemical content depends on the geographic zone from which it comes. Over 300 chemical compounds are described in various propolis origins. Among its chemical constituents are waxes, resins, balsams, oils and ether, pollen and organic material. The proportion of these substances varies and depends on the place and period of collection. Different geographic locations in the world will have different plants available to the bees in which to make propolis from and thus the differences in the medical properties of propolis.

The collected propolis in a bee hive, also known as crude propolis, in its basic composition, contains about 50% of plant resins, 30% of beeswax, 10% essential oils, 5% pollen, and 5% debris of wood and earth. Propolis also contains various organic acids, considerable amount of minerals (including, manganese, zinc, calcium, phosphorus and copper), vitamins B1, B2, B6, C and E, acids (nicotinic acid and pantothenic acid) and amino acids. Nevertheless, their presence and percentage content in propolis changes and depends on their origin, the type of plant pollen, and the species of bees that produced it. The composition of chemical compounds is responsible for the properties of propolis. Applications of propolis in medicine have been described extensively. It has antibacterial, antifungal, anti-inflammatory, anticancer, antiviral, immunostimulator, and many other properties. A wide spectrum of its reaction allows it to be used in many medical applications including dental applications. The antibacterial activity is conferred by the presence of flavonoids, aromatic acids and esters in its composition; bactericidal action results from the presence of cinnamic acid and coumarin; in vitro antiviral activity may be due to the action of flavonoids and aromatic acids derivatives.

Propolis is administered in an amount of from about 0.001 mg/kg/day body weight of the animal to 10,000 mg/kg/day body weight of the animal. Preferably, the propolis is administered in an amount of from about 0.001 mg/kg/day body weight of the animal to 1,000 mg/kg/day body weight of the animal. More preferably, the propolis is administered in an amount of about 1.4 mg/kg weight/day. The propolis may be sourced from any geographic location in the world, including the continents of South America, North America, Asia, Europe and Australia.

Propolis considerably reduces teeth caries in rats through multiple modes of action. It limits the number of microorganisms, slows down synthesis of insoluble glucans, and slows down activity of glucosyltransferase (Ikeno). Studies show that extracts from propolis limit the quantity of bacterial plaque which influences the reduction of tooth caries (Więckiewicz). The cariostatic effects of propolis may be due high quantity of fatty acids which slow down the production of acids by Streptococcus mutans and decreases the tolerance of microorganisms to acid pH.

Most of the research with propolis is used directly in the mouth in the form of ethanol- or water-based mouth rinses or in the form of toothpaste. Studies confirmed antibacterial properties of propolis in relation to pathogens of periodontitis (Santos). It has been shown that a significant reduction in plaque and in gingival index when compared to controls (Koos). There were no important side effects in soft and hard tissues of the mouth. It was also shown that propolis demonstrated high effectiveness of mouthwash containing propolis in control of dental plaque and gingivitis in humans and not observed no toxic or side effects in the administration of the rinse during 90 days (Pereira). However, an advance in the art for companion animals would be to incorporate propolis actives into a hard chew.

Propolis has the advantage of being a natural product as compared to chlorhexidine. Propolis has many therapeutic substances compatible with the metabolism of mammals in general, which reduces the possibility of causing adverse reactions to oral tissue as compared to chlorhexidine. The aqueous and alcoholic extracts of propolis do not cause irritation to the tissues and are considered safe. Studies have exhibited a no toxic effect level in mice at 1400 mg/kg weight/day. Safe dose in animals would be 1.4 mg/kg weight/day, or approximately 70 mg/day.

Process for Preparation of Plant-Based Hard Chew:

The mixture is subjected to a melting and plasticizer process in a standard extrusion device. The invention will be extruded through a star-shaped portal that would allow the final product to have ridges. The extruded product containing the antimicrobials are then cut to length and packaged for selling to the consumer. This manufacturing process allows for a unique hard chew product containing plaque reducing active ingredients for companion animals.

Hard chews for dogs are typically made through an extrusion or injection molding process, as commonly used in making plastic parts. Typically, standard hard chews have raised surfaces and ridges that allow for optimal teeth cleaning. The extrusion and injection molding process involves elevated temperatures that are required to melt the base ingredients and active ingredients in the formula.

The matrix can be formed using baking, extrusion, injection molding processes. The matrix of the invention can be made with a variety of natural or artificial ingredients. These natural ingredients can include starches from plant sources or rawhide from animal sources. Artificial ingredients can include rubber or plastics.

The characteristics of the hard chew matrix are that the product can be edible, the matrix will help clean dog teeth through the hard chewing surface and edges or ridges on the product surface, can last up to 30 minutes or more of chewing and contain antimicrobial agents that give additional health benefits and a marketing advantage to the product.

The exact hardness of the matrix will depend on the matrix ingredients and the manufacturing processes used. There are three main types of hardness measurements: scratch, indentation, and rebound. The commonly used Brinell values for measuring hardness of the matrix of the invention can range from 0.1 HBS 10/100 to 20 HBS 100/100 where "HBS", which means a hardened steel ball, the "10" is the ball diameter in millimeters and the "100" is the force in kilograms force. For reference values, softwood pine has a Brinell hardness numbers of 1.6 HBS 10/100, hardwood ranges from 2.6-7.0 HBS 10/100, while various metals can range from 5 to 900 or more.

Non-limiting examples of suitable animals include humans, dogs, cats, horses, cows, pigs, goats, and sheep, among others. The composition is preferably used with dogs.

Animal Parts as the Substrate Matrix:

The matrix of the hard chew may also be from animal sources. Examples include dried pig ears, dried rawhide, bull penis, bones and other animal parts. These animal parts can incorporate the antimicrobial actives of the invention. Active ingredients are coated on the surface of these animal parts and dried prior to chewing by the animal.

Process for Preparing Substrate Matrix for Animal-Derived Hard Chew:

The animal parts may be of a hardened matrix already. The active ingredients are solubilized in water or added as a suspension. These animal parts are then soaked in the active ingredients. The soaked animal parts are dried using heat. Previously soft texture animal parts become hardened during the heating process that dries the active ingredients onto the surface of animal part. Animal parts that are hardened to begin with are soaked with the active ingredient and dried with heat to dry the active ingredients on the surface of the animal part. Vitamins and minerals can also be incorporated onto the surface of the animal parts by solubilizing these ingredients in the same solution as the active ingredients.

Artificial Ingredients as the Substrate Matrix:

Artificial ingredients for creating chews can include rubber, polyurethane, vinyl or nylon polymer and thermoplastics. The hard chews made out of plastic-like materials can last for months; however, these are not digestible.

Process for Preparing Substrate Matrix for Hard Chew Made from Artificial Ingredients:

Artificial ingredients to form the matrix can include rubber, plastics or nylon. Active ingredients are mixed together with the non-edible ingredients during the formation of the non-edible hard chew matrix. Typically injection molding or extrusion processes, known to the art, of the mixture of non-edible ingredients and active ingredients are used to create the final product.

A typical formulation for a dog is described in Table 1:

TABLE 1

| % w/w | Ingredient |
|---|---|
| 68.88 | Potato starch |
| 5.67 | Calcium carbonate |
| 1.13 | Lecithin |
| 0.75 | Chicken liver powder |
| 0.56 | Oat fiber |
| 0.075 | Curcumin |
| 1.08 | Silver nanoparticle |
| 0.18 | Propolis |
| 10.59 | Water |
| 12.11 | Glycerol |

The nanosilver was initially mixed thoroughly into the chicken liver flavor. Then the remaining ingredients were mixed together with the previously mixed materials and extruded in a single screw extruder with vented barrel at the vent port to apply some vacuum to help remove water. The extrusion shape dye created spiral shaped product with edges. The extrudate was cut to 25 gram pieces. The extruded product pieces are placed in a dryer at 75° C. for 45 minutes. The final product after drying had a Brinell hardness value of 1.0 HBS 10/100.

Example 1

Hard Chew Formulation

A hard chew matrix comprising the ingredients listed in Table 2 below was prepared according to the steps listed above.

TABLE 2

| Amount | Item |
|---|---|
| 91 Lbs. | Potato starch (as thermal plastic base matrix) |
| 7.5 Lbs. | Calcium carbonate (for hardener of matrix) |
| 1.5 Lbs. | Lecithin (as emulsifier) |
| 1.0 Lbs. | Chicken liver powder (as flavor) |
| 0.75 Lbs. | Oat fiber (as humectant) |
| 0.1 Lbs. | Curcumin (as active) |
| 6.5 mg | 10 nm size particles of nanosilver (as active) |
| 0.25 Lbs. | Propolis (as active) |
| 14 Lbs. | Water (as plasticizer) |
| 16 Lbs. | Glycerol (as plasticizer) |

Example 2

The invention in Example 1 was given to a dog for palatability testing. It was found that the composition was chewed on and safely digested.

Example 3

The invention in Example 1 of a 25 gram size was given to a dog that was judged to have dental plaque and gum inflammation on a daily basis. After 30 days, the dog was judged to have lower dental plaque than prior to use of the invention. In addition, gum inflammation was reduced. There were no safety concerns noted.

Example 4

Bacteria collected by oral swab of the gum line and tooth from a dog with plaque was inoculated in the agar of petri dishes. Wells were punched in the cooled agar and a varying concentrations of propolis extract was placed in the wells. The petri dishes were incubated for 2 days at 37° C. It was observed that increased clearing occurred around the wells in a dose response manner with increased amounts of propolis. The results indicate that propolis has specific ability to kill bacteria associated with plaque formation in dogs.

Example 5

Bacteria collected with the oral swab of the tooth and gum line from a dog with plaque in example 4 was inoculated in a liquid broth in flasks that grows the bacteria. Varying concentrations of 10 mm size nanosilver were added to the liquid cultures and the flasks were incubated with shaking for 2 days at 37° C. It was observed that turbidity decreased with increasing concentrations of nanosilver. The results indicated that nanosilver has specific ability to kill bacteria associated with plaque formations in dogs.

Example 6

Actives were solubilized in water as described in Table 3 to create a suspension:

TABLE 3

| % w/w | Active Ingredient |
|---|---|
| 0.075 | Curcumin |
| 1.08 | Silver 10 nm nanoparticle |
| 0.18 | Propolis |

Pig ears were soaked in the actives solution for 8 hours. The pig ears were placed on pans in an oven at 90° C. until dried. The active ingredients form a coating on the surface of the dried pig ear matrix. The coated pig ear was given to a dog to chew on and was consumed avidly.

While this invention may be embodied in many forms, what is described in detail herein is a specific preferred embodiment of the invention. The present disclosure is an exemplification of the principles of the invention is not intended to limit the invention to the particular embodiments illustrated. It is to be understood that this invention is not limited to the particular examples, process steps, and materials disclosed herein as such process steps and materials may vary somewhat. It is also understood that the terminology used herein is used for the purpose of describing particular embodiments only and is not intended to be limiting since the scope of the present invention will be limited to only the appended claims and equivalents thereof.

Any version of any component or method step of the invention may be used with any other component or method step of the invention. The elements described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference in their entirety to the same extent as if each individual reference were specifically and individually indicated as being incorporated by reference. In case of conflict between the present disclosure and the incorporated references, the present disclosure controls.

The devices, methods, compounds and compositions of the present invention can comprise, consist of, or consist essentially of the essential elements and limitations described herein, as well as any additional or optional steps, ingredients, components, or limitations described herein or otherwise useful in the art.

While this invention may be embodied in many forms, what is described in detail herein is a specific preferred embodiment of the invention. The present disclosure is an exemplification of the principles of the invention is not intended to limit the invention to the particular embodiments illustrated. It is to be understood that this invention is not limited to the particular examples, process steps, and materials disclosed herein as such process steps and materials may vary somewhat. It is also understood that the terminology used herein is used for the purpose of describing particular embodiments only and is not intended to be limiting since the scope of the present invention will be limited to only the appended claims and equivalents thereof.

BIBLIOGRAPHY

Mali, A. M. et al. "Comparative evaluation of 0.1% turmeric mouthwash with 0.2% chlorhexidine gluconate in prevention of plaque and gingivitis: A clinical and microbiological study." *J. Indian Soc. Periodontol.* 2012 July; 16(3): 386-91.

Besinis A, et al. "Inhibition of biofilm formation and antibacterial properties of a silver nano-coating on human dentine." *Nanotoxicology.* 2014 November; 8(7):745-54.

Grindel B. and I. Olsen. "The role of viruses in oral disease." *Journal of Oral Microbiology* 2010. 2: 2127

Galdiero, S. et al. "Silver Nanoparticles as Potential Antiviral Agents." *Molecules* 2011, 16, 8894-8918.

Ikeno K., et al. "Effects of propolis on dental caries in rats," *Caries Research, vol.* 25, no. 5, pp. 347-351, 1991.

Koo H, et al. "Effect of a mouth rinse containing selected propolis on 3-day dental plaque accumulation and polysaccharide formation." *Caries Research* 2002; 36(6):445-448.

Kvitek L., et al. "Antibacterial activity and toxicity of silver-nanosilver versus ionic silver." *Journal of Physics: Conference Series* 304 (2011)

Kim, Jun Sung, et al. "Antimicrobial effects of silver nanoparticles." *Nanomedicine: Nanotechnology, Biology, and Medicine* 3 (2007) 95-101.

Mali, A. M., et al. "Comparative evaluation of 0.1% turmeric mouthwash with 0.2% chlorhexidine gluconate in prevention of plaque and gingivitis: A clinical and microbiological study." *J. Indian Soc. Periodontol.* 2012 July; 16(3):386-91. PMID: 23162334.

Pereira E M, et al. "Clinical Evidence of the Efficacy of a Mouthwash Containing Propolis for the Control of Plaque and Gingivitis: A Phase II Study." *Evidence-Based Complementary and Alternative Medicine* 2011; 2011: 750249.

Sangeeta, Muglikar, et al. "Efficacy of curcumin in the treatment of chronic gingivitis: a pilot study." *Oral Health Prev. Dent.* 2013; 11(1):81-6.

Stebounova L V, et al. "Nanosilver induces minimal lung toxicity or inflammation in a subacute murine inhalation model." *Part. Fibre Toxicol.* 2011 Jan. 25; 8(1):5. doi: 10.1186/1743-8977-8-5.

Santos V R. "Propolis: Alternative Medicine for the Treatment of Oral Microbial Diseases" http://dx.doi.org/10.5772/54003.

Więckiewicz W., et al. "Does Propolis Help to Maintain Oral Health?" *Evidence-Based Complementary and Alternative Medicine.* Volume 2013 (2013), Article ID 351062, 8 pages. http://dx.doi.org/10.1155/2013/351062

Waghmare P F, et al. "Comparative evaluation of turmeric and chlorhexidine gluconate mouthwash in prevention of plaque formation and gingivitis: a clinical and microbiological study." *J. Contemp. Dent. Pract.* 2011; 12(4):221-4.

What is claimed is:

1. A dental hard chew supplement for treating tooth and gum health issues in a mammal comprising therapeutically effective amounts of a plurality of antimicrobial active ingredients present in and throughout a hard chew substrate matrix, wherein the hard chew substrate matrix is an edible, digestible matrix comprising an extruded or injection molded mixture of plant starch and the plurality of antimicrobial active ingredients, wherein the plurality of antimicrobial active ingredients comprise curcumin and propolis.

2. The dental hard chew supplement of claim 1 wherein the plurality of antimicrobial active ingredients further comprises one or more of: metal particles selected from the group consisting of silver, gold, aluminum, copper, and zinc.

3. The dental hard chew supplement of claim 1, wherein the antimicrobial active ingredient further comprises silver nanoparticles of elemental silver, silver ions, or silver salts in an amount of from about 1 mg/kg body weight of the mammal to about 30 mg/kg body weight of the mammal.

4. The dental hard chew supplement of claim 1 wherein the antimicrobial active ingredient comprises curcumin in an amount of from about 10 mg/kg body weight of the mammal to about 20 mg/kg body weight of the mammal.

5. The dental hard chew supplement of claim 1 wherein the antimicrobial active ingredient comprises propolis in an amount of from about 0.001 mg/kg body weight of the mammal to about 10,000 mg/kg body weight of the mammal.

6. The dental hard chew supplement of claim 1 wherein the antimicrobial active ingredient further comprises silver salts in an amount of from about 0.5 mg/kg body weight of the mammal to about 9 mg/kg of body weight of the mammal.

7. The dental hard chew supplement of claim 1 further comprising vitamins selected from the group consisting of vitamin A, vitamin C, vitamin D, vitamin E, vitamin K, vitamin B1, vitamin B2, vitamin B3, vitamin B5, vitamin B6, vitamin B7, vitamin B9, and vitamin B12, wherein the vitamins are present in an amount from about 0.5% to about 1% w/w of the hard chew substrate matrix.

8. The dental hard chew supplement of claim 1 further comprising minerals in a therapeutically effective amount selected from the group consisting of zinc, manganese, copper, and molybdenum.

9. The dental hard chew supplement of claim 1 further comprising a flavoring selected from the group consisting of xylose, ribose, sucrose, mannose, galactose, fructose, dextrose, maltose, molasses, honey, maple syrup, carob, peanuts, garlic, parsley, celery, peppermint, spearmint, anise oil, spearmint oil, peppermint oil, cinnamon oil, wintergreen oil, lemon oil, orange oil, grape oil, lime oil, grapefruit oil, apple, strawberry, cherry, pineapple, and chicken liver, wherein the flavoring is included in an amount of from about 0% to about 20% w/w of the hard chew substrate matrix.

10. The dental hard chew supplement of claim 9, wherein the flavoring is present in an amount of from about 4% to about 6% w/w of the hard chew substrate matrix.

11. The dental hard chew supplement of claim 1 further comprising omega-3 and omega-6 polyunsaturated fatty acids in therapeutically effective amounts.

12. The dental hard chew supplement of claim 1 wherein the hard chew substrate matrix comprises a carrier base comprising components selected from the group consisting of powders of flour, an emulsifier, a softening agent, and water in a combination and in amounts effective to confer a hard chew substrate matrix.

13. The dental hard chew supplement of claim 12 wherein the powders of flour are selected from the group consisting of soy flour, wheat gluten, pregel wheat flour, wheat feed flour, corn starch, soy protein concentrate, oat, barley, brown rice, dried whey powder, liver powder, carrot powder, cherry powder, pineapple powder, and alfalfa herb powder, wherein the powders of flour are present in an amount from about 1-50% w/w of the hard chew substrate matrix.

14. The dental hard chew supplement of claim 1 wherein the plant starch is selected from the group consisting of cereal and grains or flours obtained upon grinding a cereal selected from the group consisting of corn, oat, wheat, milo, barley, rice, and tuberous foodstuff, wherein the starch is included in the hard chew substrate matrix in an amount of from about 1 to 50% w/w of the hard chew substrate matrix.

15. The dental hard chew supplement of claim 12 wherein the emulsifier is selected from the group consisting of lecithin, polyoxyethylated castor oil, polyoxyethylated sorbitan monooleate, sorbitan monostearate, ethyl alcohol, glycerol monostearate, polyoxyethyl stearate, an alkylphenol polylglycol ether, an ampholytic surfactant, and an anionic surfactant, wherein the emulsifier is present in an amount ranging from about 0 to 20% w/w of the hard chew substrate matrix.

16. The dental hard chew supplement of claim 12 wherein the water is present in an amount ranging from 0 to 50% w/w of the hard chew substrate matrix.

17. The dental hard chew supplement of claim 1 wherein the hard chew substrate matrix further comprises an animal-source product.

18. The dental hard chew supplement of claim 17 wherein the animal-source product is selected from the group consisting of bull penis, hardened (dried) animal ligament or rawhide, deer antler, cattle horn, fish skin, pig ear, cow hoof, and animal bone.

19. The dental hard chew supplement of claim 1 wherein the hard chew substrate matrix further comprises a non-digestible artificial ingredient selected from the group consisting of rubber, polyurethane, vinyl polymer, nylon polymer, and thermoplastic.

20. The dental hard chew supplement of claim 1 wherein the mammal is selected from the group consisting of canine and feline.

\* \* \* \* \*